(12) United States Patent
Nappa et al.

(10) Patent No.: US 8,044,251 B2
(45) Date of Patent: Oct. 25, 2011

(54) PROCESS FOR THE PREPARATION OF HALO-OLEFINS

(75) Inventors: Mario Joseph Nappa, Newark, DE (US); Xuehui Sun, Swedesboro, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/755,671

(22) Filed: Apr. 7, 2010

(65) Prior Publication Data
US 2010/0268001 A1    Oct. 21, 2010

Related U.S. Application Data

(60) Provisional application No. 61/170,123, filed on Apr. 17, 2009.

(51) Int. Cl.
*C07C 17/00*    (2006.01)
*C07C 17/10*    (2006.01)
(52) U.S. Cl. .................................... 570/158; 570/230
(58) Field of Classification Search ............. 570/158, 570/230
See application file for complete search history.

(56) References Cited

U.S. PATENT DOCUMENTS

| 4,560,759 A | 12/1985 | Hiratani |
| 7,164,050 B2 | 1/2007 | Cottrell et al. |

FOREIGN PATENT DOCUMENTS

| EP | 1801090 | 6/2007 |
| RU | 2272017 | 3/2006 |
| WO | 2006108331 | 11/2005 |

OTHER PUBLICATIONS

CN 1566048 abstract, Xu et al, 1,2-dichloro-2,2-difluoroethane, 2003.*

* cited by examiner

*Primary Examiner* — Jafar Parsa

(57) ABSTRACT

Described is a process for preparing a halo-olefin comprising contacting a halogenated hydrocarbon with a metal dehalogenating agent, in a solvent, in the presence of a phase transfer catalyst, under conditions sufficient to dehalogenate said halogenated hydrocarbon to produce a product stream comprising said halo-olefin. In one embodiment, the halogenated hydrocarbon is trifluorotrichloroethane and the halo-olefin is chlorotrifluoroethylene.

11 Claims, No Drawings

PROCESS FOR THE PREPARATION OF HALO-OLEFINS

BACKGROUND INFORMATION

1. Field of the Disclosure

This disclosure relates in general to methods of synthesis of fluorinated olefins.

2. Description of the Related Art

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a and HFC-125 being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins are believed to meet both goals. Thus there is a need for manufacturing processes that provide halogenated hydrocarbons and fluoroolefins that contain no chlorine that also have a low global warming potential.

SUMMARY

Described is a process for preparing a halo-olefin comprising contacting a halogenated hydrocarbon with a metal dehalogenating agent, in a solvent, in the presence of a phase transfer catalyst, under conditions sufficient to dehalogenate said halogenated hydrocarbon to produce a product stream comprising said halo-olefin. In one embodiment, the halogenated hydrocarbon is trifluorotrichloroethane and the halo-olefin is chlorotrifluoroethylene.

The foregoing general description and the following detailed description are exemplary and explanatory only and are not restrictive of the invention, as defined in the appended claims.

DETAILED DESCRIPTION

Disclosed is a process for preparing a haloolefin comprising: contacting a halogenated hydrocarbon with a metal dehalogenating agent in a solvent in the presence of a phase transfer catalyst under conditions sufficient to dehalogenate said halogenated hydrocarbon to produce a product stream comprising said halo-olefin. In one embodiment, the halo-olefin is selected from the group consisting of chlorotrifluoroethylene, tetrafluoroethylene, difluoroethylene and vinyl chloride. In one embodiment, the halogenated hydrocarbon is selected from the group consisting of trichlorotrifluoroethane, dichlorotetrafluoroethane, dichlorodifluoroethane and trichloroethane. In one embodiment, the halo-olefin is chlorotrifluoroethylene and the halogenated hydrocarbon is trichlorotrifluoroethane. In one embodiment, presence of a phase transfer catalyst increases the yield of the halo-olefin, and reduces the amount of side reaction products.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

Before addressing details of embodiments described below, some terms are defined or clarified.

For purposes of the present invention, a phase transfer catalyst is a substance that facilitates the transfer of ionic compounds (e.g., reactants or components) into an organic phase. The phase transfer catalyst facilitates the reaction of these dissimilar and incompatible components. While various phase transfer catalysts may function in different ways, their mechanism of action is not determinative of their utility in the present.

As used herein, metal dehalogenating agent refers to a metal element which, when reacted with a halogenated hydrocarbon, effects the removal of halogen atoms from adjacent carbon atoms in a reductive fashion, resulting in a double bond between the two adjacent carbon atoms.

In one embodiment, the metal dehalogenating agent is a metal selected from the group consisting of tin, magnesium, zinc, iron and aluminum. In one embodiment, the metal dehalogenating agent is zinc. Such agents typically are available in various grades and various particle sizes. In general, smaller particle sizes have greater amounts of surface area, with correspondingly greater rates of reaction. Conversely, smaller particle sizes are often more difficult to handle and transfera (although size is not particularly crucial). In one embodiment, the metal dehalogenating agent is sieved through a 40 mesh screen, to leave a maximum particle size of 420 microns. In another embodiment, the metal dehalogenating agent is sieved through a 100 mesh screen, to leave a maximum particle size of 150 microns.

In one embodiment, the metal dehalogenating agent is mixed with a solvent to form a non-homogenous mixture. In another embodiment, the metal dehalogenating agent is mixed with a solvent to form a homogenous mixture. In one embodiment, the solvent should be miscible with the halogenated hydrocarbon starting material and also capable of dissolving the metal halide which is formed in the dehalogenation reaction. In one embodiment, the solvent is selected from methanol, ethanol, acetonitrile and tetrahydrofuran. In another embodiment, the solvent is methanol.

In one embodiment an equimolar amount of metal dehalogenating agent relative to halogenated hydrocarbon is used. In another embodiment, 1.05 moles of metal dehalogenating agent per mole of halogenated hydrocarbon are used. In yet another embodiment, 1.1 moles of metal dehalogenating agent per mole of halogenated hydrocarbon are used. In yet another embodiment, 0.9 moles of metal dehalogenating agent per mole of halogenated hydrocarbon are used.

In one embodiment, the halogenated hydrocarbon starting material can be dehalogenated under conditions suitable to produce a halo-olefin. In one embodiment, the dehalogenation reaction is conducted at a temperature between 50° C. and 150° C. In another embodiment, the dehalogenation reaction is conducted at a temperature between 50° C. and 100° C.

In one embodiment, the dehalogenation reaction is conducted in a batch type process. In another embodiment, the dehalogenation reaction is conducted in a continuous type process. In one embodiment of a batch type process, a slurry of metal dehalogenating agent is introduced into a reactor to initiate the reaction. The slurry is admixed with the halogenated hydrocarbon, the metal dehalogeation agent and solvent prior to, simultaneously with, or subsequent to the addition of one or more of the components of the process. In another embodiment, the slurry is admixed prior to the addition of the halogenated hydrocarbon by any convenient means.

The phase transfer catalyst can be ionic or neutral and is selected from the group consisting of crown ethers, onium salts, cryptates and polyalkylene glycols and derivatives thereof, as well as mixtures thereof. An effective amount of the phase transfer catalyst should be used in order to effect the desired reaction; such an amount can be determined by limited experimentation once the reactants, process conditions and phase transfer catalyst are selected. The effective amount may vary, depending on the particular type of phase transfer catalyst being applied.

Crown ethers are cyclic molecules in which ether groups are connected by dimethylene linkages; the compounds form a molecular structure that is believed to be capable of "receiving" or holding the alkali metal ion of the hydroxide and to thereby facilitate the reaction. Particularly useful crown ethers include 18-crown-6, especially in combination with potassium hydroxide; 15-crown-5, especially in combination with sodium hydroxide; 12-crown-4, especially in combination with lithium hydroxide. Derivatives of the above crown ethers are also useful, e.g., dibenzo-18-crown-6, dicyclohexano-18-crown-6, and dibenzo-24-crown-8 as well as 12-crown-4. Other polyethers particularly useful for alkali metal compounds, and especially for lithium, are described in U.S. Pat. No. 4,560,759 which is incorporated herein by reference to the extent permitted. Other compounds analogous to the crown ethers and useful for the same purpose are compounds which differ by the replacement of one or more of the oxygen atoms by other kinds of donor atoms, particularly N or S, such as hexamethyl-[14]-4,11-diene$N_4$.

Onium salts include quaternary phosphonium salts and quaternary ammonium salts that may be used as the phase transfer catalyst in the process of the present invention; such compounds can be represented by the following formulas I and II:

$$R^1R^2R^3R^4P^{(+)}X'^{(-)} \quad (I)$$

$$R^1R^2R^3R^4N^{(+)}X'^{(-)} \quad (II)$$

wherein each of $R_1$, $R_2$, $R_3$ and $R_4$, which may be the same or different, is an alkyl group, an aryl group or an aralkyl group, and X' is a halogen atom. Specific examples of these compounds include tetramethylammonium chloride, tetramethylammonium bromide, benzyltriethylammonium chloride, methyltrioctylammonium chloride (available commercially under the brands Aliquat 336 and Adogen 464), tetra-n-butylammonium chloride, tetra-n-butylammonium bromide, tetra-n-butylammonium hydrogen sulfate, tetra-n-butylphosphonium chloride, tetraphenylphosphonium bromide, tetraphenylphosphonium chloride, triphenylmethylphosphonium bromide and triphenylmethylphosphonium chloride. Among them, benzyltriethylammonium chloride is preferred for use under strongly basic conditions. Other useful compounds within this class of compounds include those exhibiting high temperature stabilities (e.g., up to about 200.degree. C.) and including 4-dialkylaminopyridinium salts such as tetraphenylarsonium chloride, bis[tris(dimethylamino)phosphine]iminium chloride and tetratris[tris(dimethylamino)phosphinimino]phosphonium chloride; the latter two compounds are also reported to be stable in the presence of hot, concentrated sodium hydroxide and, therefore, can be particularly useful.

Polyalkylene glycol compounds useful as phase transfer catalysts can be represented by the formula:

$$R^6O(R^5O)_tR^7 \quad (III)$$

wherein $R_5$ is an alkylene group, each of $R_6$ and $R_7$, which may be the same or different, is a hydrogen atom, an alkyl group, an aryl group or, an aralkyl group, and t is an integer of at least 2. Such compounds include, for example glycols such as diethylene glycol, triethylenre glycol, tetraethylene glycol, pentaethylene glycol, hexaethylene glycol, diisopropylene glycol, dipropylene glycol, tripropylene glycol, tetrapropylene glycol and tetramethylene glycol, and monoalkyl ethers such as monomethyl, monoethyl, monopropyl and monobutyl ethers of such glycols, dialkyl ethers such as tetraethylene glycol dimethyl ether and pentaethylene glycol dimethyl ether, phenyl ethers, benzyl ethers, and polyalkylene glycols such as polyethylene glycol (average molecular weight about 300) dimethyl ether, polyethylene glycol (average molecular weight about 300) dibutyl ether, and polyethylene glycol (average molecular weight about 400) dimethyl ether. Among them, compounds wherein both $R_6$ and $R_7$ are alkyl groups, aryl groups or aralkyl groups are preferred.

Cryptates are another class of compounds useful in the present as phase transfer catalysts. These are three-dimensional polymacrocyclic chelating agents that are formed by joining bridgehead structures with chains that contain properly spaced donor atoms. For example, bicyclic molecules that result from joining nitrogen bridgeheads with chains of (—$OCH_2CH_2$—) groups as in 2.2.2-cryptate (4,7,13,16,21, 24-hexaoxa-1,10-diasabicyclo-(8.8.8)hexacosane; available under the brand names cryptand 222 and Kryptofix 222). The donor atoms of the bridges may all be O, N, or S, or the compounds may be mixed donor macrocycles in which the bridge strands contain combinations of such donor atoms.

Combinations of phase transfer catalysts from within one of the groups described above may also be useful as well as combinations or mixtures from more than one group, for example, crown ethers and oniums, or from more than two of the groups, e.g., quaternary phosphonium salts and quaternary ammonium salts, and crown ethers and polyalkylene glycols.

In one embodiment, the phase transfer catalyst is an onium salt. In another embodiment, the phase transfer catalyst is selected from the group consisting of tetramethylammonium chloride, tetramethylammonium bromide, benzyltriethylammonium chloride, methyltrioctylammonium chloride, tetra-n-butylammonium chloride, tetra-n-butylammonium bromide, tetra-n-butylammonium hydrogen sulfate, tetra-n-butylphosphonium chloride, tetraphenylphosphonium bromide, tetraphenylphosphonium chloride, triphenylmethylphosphonium bromide and triphenylmethylphosphonium chloride. In yet another embodiment, the phase transfer catalyst is a methyltrioctylammonium halide. In yet another embodiment, the phase transfer catalyst is tetrabutylammonium bromide.

In one embodiment, an effective amount of phase transfer catalyst is 1 gram of tetrabutylammonium bromide per 50 grams of halogenated hydrocarbon. In another embodiment, an effective amount of phase transfer catalyst is 1 gram of tetrabutylammonium bromide per 100 grams of halogenated hydrocarbon. In another embodiment, an effective amount of phase transfer catalyst is 1 gram of tetrabutylammonium bromide per 200 grams of halogenated hydrocarbon. In another embodiment, an effective amount of phase transfer catalyst is 1 gram of tetrabutylammonium bromide per 25 grams of halogenated hydrocarbon.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Example 1

Example 1 demonstrates the conversion of CFC-113 to chlorotrifluoroethylene (CTFE) with zinc.

A 210 mol hastelloy shaker tube was charged with 16.4 g (0.25 mol) of Zinc powder, 50 g methanol and 46.9 g (0.25 mol) CFC-113. The zinc powder had been activated under nitrogen, dried in a dry box and then sieved through a 40 mesh screen to remove large particle agglomerates. Then the reactor was pressured up with $N_2$ and vented $N_2$ off for two times. After that the reactor was cooled down to −70° C. and pulled vacuum slightly. The reaction mix was heated and agitated at 65° C. for 3 hr. The pressure of the reactor increased to 227 psig from 179 psig at 65° C. After reactor was cooled down to room temperature, the vapor phase of the reaction was analyzed by GC-MS. The data is reported by area percent of GC-MS (methanol is excluded from integration). The analysis of liquid phase of the reactor show the conversion of 113 is 90.6%.

TABLE 1

| (vapor phase) | | |
|---|---|---|
| Compound | | GC-MS area % |
| CF2=CH2 | 1,1-difluoroethylene | 0.056 |
| CF2=CFH | Trifluoroethylene | 1.25 |
| CF2=CFCl | Chlorotrifluoroethylene (CTFE) | 97.124 |
| CF2=CHCl | 1-chloro-2,2-difluoroethylene | 0.024 |

TABLE 1-continued

| (vapor phase) | | |
|---|---|---|
| Compound | | GC-MS area % |
| CClF2—CClHF | 1,2-dichloro-1,1,2-trifluoroethane | 0.772 |
| CF2ClCFCl2 | 1,1,2-trichloro-1,2,2-trifluoroethane (CFC-113) | 0.764 |
| unknown | | 0.01 |

Example 2

Example 2 demonstrates the conversion of CFC-113 to CTFE with zinc in the presence of tetrabutylammonium bromide (TBAB).

A 210 mol hastelloy shaker tube was charged with 16.4 g (0.25 mol) of Zinc powder, 50 g methanol, 46.9 g (0.25 mol) CFC-113 and 1 g TBAB. The zinc powder had been activated under nitrogen, dried in a dry box and then sieved through a 40 mesh screen to remove large particle agglomerates. Then the reactor was pressured up with $N_2$ and vented $N_2$ off for two times. After that the reactor was cooled down to −70° C. and pulled vacuum slightly. The reaction mix was heated and agitated at 65° C. for 3 hr. The pressure of the reactor increased to 229 psig from 205 psig at 65° C. After reactor was cooled down to room temperature, the vapor phase of the reaction was analyzed by GC-MS. The data is reported by area percent of GC-MS (methanol is excluded from integration). The analysis of liquid phase of the reactor show the conversion of CFC-113 is 98.5%

TABLE 2

| (vapor phase) | | |
|---|---|---|
| Compound | | GC-MS area % |
| CF2=CH2 | 1,1-difluoroethylene | 0.009 |
| CF2=CFH | Trifluoroethylene | 0.28 |
| CF2=CFCl | Chlorotrifluoroethylene | 99.065 |
| CF2=CHCl | 1-chloro-2,2-difluoroethylene | 0.045 |
| CClF2—CClHF | 1,2-dichloro-1,1,2-trifluoroethane | 0.49 |
| CF2ClCFCl2 | 1,1,2-trichloro-1,2,2-trifluoroethane | 0.112 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for preparing a haloolefin comprising:
   contacting a halogenated hydrocarbon with a metal dehalogenating agent, in a solvent, in the presence of a phase transfer catalyst, under conditions sufficient to dehalogenate said halogenated hydrocarbon to produce a product stream comprising said haloolefin.

2. The process of claim 1, wherein said haloolefin is selected from the group consisting of chlorotrifluoroethylene, tetrafluoroethylene, difluoroethylene and vinyl chloride.

3. The process of claim 2 wherein said halo-olefin in chlorotrifluoroethylene.

4. The process of claim 1, wherein said halogenated hydrocarbon is selected from the group consisting of trichlorotrifluoroethane, trichloroethane, dichlorodifluorethane and dichlorotetrafluoroethane.

5. The process of claim 4, wherein said halogenated hydrocarbon is trichlorotrifluoroethane.

6. The process of claim 1, wherein said dehalogenating agent is selected from the group consisting of zinc, tin, manganesium, iron, and aluminum.

7. The process of claim 6, wherein said dehalogenating agent is zinc.

8. The process of claim 1, wherein said phase transfer catalyst is selected from the group consisting of crown ethers, onium salts, cryptates and polyalkylene glycols and derivatives thereof, and mixtures thereof.

9. The process of claim 8, wherein said phase transfer catalyst is an onium salt.

10. The process of claim 8, wherein said phase transfer catalyst is a quaternary ammonium salt.

11. The process of claim 10, wherein said quaternary ammonium salt is a tetrabutylammonium bromide.

* * * * *